(12) United States Patent
Wang et al.

(10) Patent No.: US 11,366,092 B2
(45) Date of Patent: Jun. 21, 2022

(54) AUTOMATIC FABRIC FOLDING DEVICE

(71) Applicant: Jiangnan University, Jiangsu (CN)

(72) Inventors: Lei Wang, Jiangsu (CN); Weidong Gao, Jiangsu (CN); Fengxin Sun, Jiangsu (CN); Xuerong Fan, Jiangsu (CN)

(73) Assignee: JIANGNAN UNIVERSITY, Wuxi (CN)

( * ) Notice: Subject to any disclaimer, the term of this patent is extended or adjusted under 35 U.S.C. 154(b) by 366 days.

(21) Appl. No.: 16/536,805

(22) Filed: Aug. 9, 2019

(65) Prior Publication Data

US 2020/0232965 A1 Jul. 23, 2020

(30) Foreign Application Priority Data

Jan. 18, 2019 (CN) .......................... 201910048121.6

(51) Int. Cl.
*G01N 33/36* (2006.01)
*D06F 89/00* (2006.01)

(52) U.S. Cl.
CPC ........... *G01N 33/367* (2013.01); *D06F 89/00* (2013.01)

(58) Field of Classification Search
CPC ...... G01N 33/36; G01N 33/367; D06F 89/00; D06F 89/005

USPC .......................................................... 73/159
See application file for complete search history.

(56) References Cited

U.S. PATENT DOCUMENTS 3,507,149 A * 4/1970 Markezich ............. G01N 33/36
73/159
2020/0326323 A1* 10/2020 Wang ................. G06K 9/00711

FOREIGN PATENT DOCUMENTS

CN 107121538 A * 9/2017
CN 111066839 B * 8/2021

* cited by examiner

*Primary Examiner* — Nathaniel J Kolb
(74) *Attorney, Agent, or Firm* — Muncy, Geissler, Olds & Lowe, P.C.

(57) ABSTRACT

An automatic fabric folding device has a rotating mechanism, an automatic folding mechanism and a crease generating mechanism. The automatic folding mechanism is located below the finger cylinder on one side of the rotating mechanism, and the finger cylinder on the other side of the automatic folding mechanism is fixed with a crease generating mechanism. The two rotating cylinders are central symmetrical with the rotating arm. This accurately controls the bending and folding of the fabric sample through the automatic control technology, and realizes the automatic detection of the fabric crease recovery process. By mechanical and numerical control technology, the parts to be measured are effectively prevented from interference by human factors, and the detection accuracy is improved.

2 Claims, 3 Drawing Sheets

AUTOMATIC FABRIC FOLDING DEVICE

TECHNICAL FIELD

The invention belongs to the field of textile performance testing, and relates to an automatic fabric folding device and detection method.

BACKGROUND TECHNOLOGY

The crease recovery property of fabrics is regarded as one of the key properties in fabric quality testing. The specified size samples are manual cut and folded into the pressing device. When a certain pressure time is reached, the samples are transferred to the measuring device artificially and the results of the crease recovery angle test are obtained by artificial reading. In the process of testing, the samples are repeatedly touched by human, which causes large errors in the test results. Although some of the existing testers for evaluating fabric crease recovery performance have realized the functions of automatic pressing and pressure relief, manual operation is still needed to make the sample form a bending and folding state. In the operation, it is unavoidable that the state of the fabric is affected by manual factors, especially the position where the creases will emerge and this will cause unstable and unreliable experimental results. In view of the above shortcomings, the present invention provides a novel fabric automatic precise folding method, greatly improving the automation extent of the fabric performance testing equipment and ensuring that the fabrics are not disturbed by human factors in the process of measuring the crease recovery performance.

SUMMARY OF THE INVENTION

The invention provides an automatic fabric folding device and detection method, which automatically folds the two sides of a flat fabric to produce creases to assess the crease recovery performance of the fabric.

The technical solution of the present invention is as follows:

The automatic fabric folding device comprises a rotating mechanism, an automatic folding mechanism and a crease generating mechanism. The automatic folding mechanism is located below the finger cylinder on one side of the rotating mechanism, and a second cylinder on the other side of the automatic folding mechanism is adjacent to a crease generating mechanism. Two sets of automatic fabric folding device are set symmetrically on the horizontal plane, which can simultaneously fold fabrics to improve efficiency.

The rotating mechanism comprises a first turntable, a first metal sheet, a first finger cylinder, a first rotating cylinder, a second rotating cylinder, a second finger cylinder and a second metal sheet.

The rotating arm is fixed above the first turntable. The two ends of the rotating arm are respectively fixed with the first rotating cylinder and the second rotating cylinder. The two rotating cylinders are centrally symmetrical with the rotating arm. The first turntable rotates to drive the two rotating cylinders to rotate. an output end of the first rotating cylinder is fixed with the first finger cylinder, and an output end of the second rotating cylinder is fixed with the second finger cylinder. The first rotating cylinder is adapted to rotate the first finger cylinder between a vertical and a horizontal orientation, and the second rotating cylinder is adapted to rotate the second finger cylinder between a vertical and a horizontal orientation.

The finger cylinder can clamp the sample on both sides of the metal sheet, and the metal sheet is in the middle of the folding sample to prevent the sample from boning. The rotating cylinder makes the sample clamped by the finger cylinder rotate 90°, forming a state that the crease is perpendicular to the horizontal plane. Thus, the test results are not affected by the weight of the sample when the recovery angle is tested. The turntable transports the sample from the automatic folding mechanism to the crease generating mechanism.

The automatic folding mechanism comprises a first servo motor, a first lifting platform, a first vacuum turning platform and a first sample positioning block.

The first servo motor and the first sample positioning block are fixed on the upper surface of the first lifting platform. The first sample positioning block is located at the output end of the first servo motor and below the first finger cylinder. The output end of the first servo motor is fixed with a first vacuum turning platform, and the other ends of the first and second vacuum turning platforms are fixed with a synchronous gear separately. The first and second turning platforms are driven by the first servo motor through the synchronous gears. The first and second vacuum turning platforms are horizontally fixed above the first sample positioning block, and the metal sheets are vertically fixed between them. The first vacuum turning platform is square block, with air suction holes on one side of the square block, and the air suction holes are connected with the air suction fan, and the sample is placed on the first vacuum turning platform. The suction holes absorb the two sides of the sample to make the two sides of the sample aligned during the turning process of the first vacuum turning platform to prepare for accurate folding of the sample.

The first lifting platform makes the sample placed on the surface of the first vacuum turning platform rise to the position where the first finger cylinder can clamp the sample. The vacuum turning platform can effectively adsorb both ends of the sample, thus forming the bending shape of the sample, and the sample positioning block plays the role of fixing the position of the sample.

The crease generating mechanism comprises the first pressing cylinder and the first electromagnetic support block. The first pressing cylinder and the first electromagnetic support block are fixed on the top of the crease bracket. The first pressing cylinder and the first electromagnetic support block are set correspondingly and at the level of the finger cylinder of the rotating mechanism. When the finger cylinder holds the metal sheet and rotates 90° vertically, the metal sheet is located in the gap between the first pressing cylinder and the first electromagnetic support block. Pressing cylinder is used to exert constant pressure on the sample. Electromagnetic support block is used to absorb the metal sheet, so that one side of the sample is clamped between the metal sheet and the electromagnetic support block, which plays the role of fixing the sample in the recovery testing process.

Furthermore, the vacuum turning platform has three parallel suction holes, which are located at the edge of the vacuum turning platform.

The detection method of automatic fabric folding device is as follows:

Step 1: Place the fabric sample on the surface of the first vacuum turning platform and open the measuring machine.

Step 2: The suction holes of the first vacuum turning platform absorb both ends of the sample.

Step 3: The first lifting platform rises, and the first servo motor drives the synchronous gear, which makes the first vacuum turning platform turn over and drives the sample to form a folding state. The first metal sheet is located between the samples.

Step 4: The first finger cylinder holds both sides of the sample folded together.

Step 5: The first vacuum turning platform closes the vacuum, the first servo motor drives the first vacuum turning platform to turn in reverse to restore the open state, and the first lifting platform descends.

Step 6: The first turntable rotates 180°, and the sample is held by the first finger cylinder and transported to the crease generating mechanism.

Step 7: The first rotating cylinder rotates 90°. The sample is placed between the first pressing cylinder and the first electromagnetic support block. The first electromagnetic support block is opened so that the first electromagnetic support block can absorb the first metal sheet. Then part of the sample is stably clamped on the crease generating mechanism.

Step 8: The first pressing cylinder is started to pressurize the sample. At the same time, the first finger cylinder is released to stop holding the sample.

Step 9: When the pressure time is reached, the first pressure cylinder is released, the first electromagnetic support block still absorbs the first metal sheet, the fabric sample is in the state of free recovery of creases, and the camera records the state of sample recovery process.

Step 10: When the fabric sample is restored freely for a period of time, the electromagnet of the first electromagnetic support block is released, and the first rotating cylinder rotates 90° to return to its initial state.

Step 11: When the first lifting platform descends, the next sample can be placed on the upper surface of the first vacuum turning platform. Repeat steps 2 to 10.

The beneficial effects of the present invention are as follows:

The present invention accurately controls the bending and folding of the fabric sample by the automatic control technology, and realizes the automatic detection of the fabric crease recovery process. By means of mechanical and numerical control technology, the parts to be measured are effectively prevented from interference by human factors, and the detection accuracy is improved.

Figure 1:
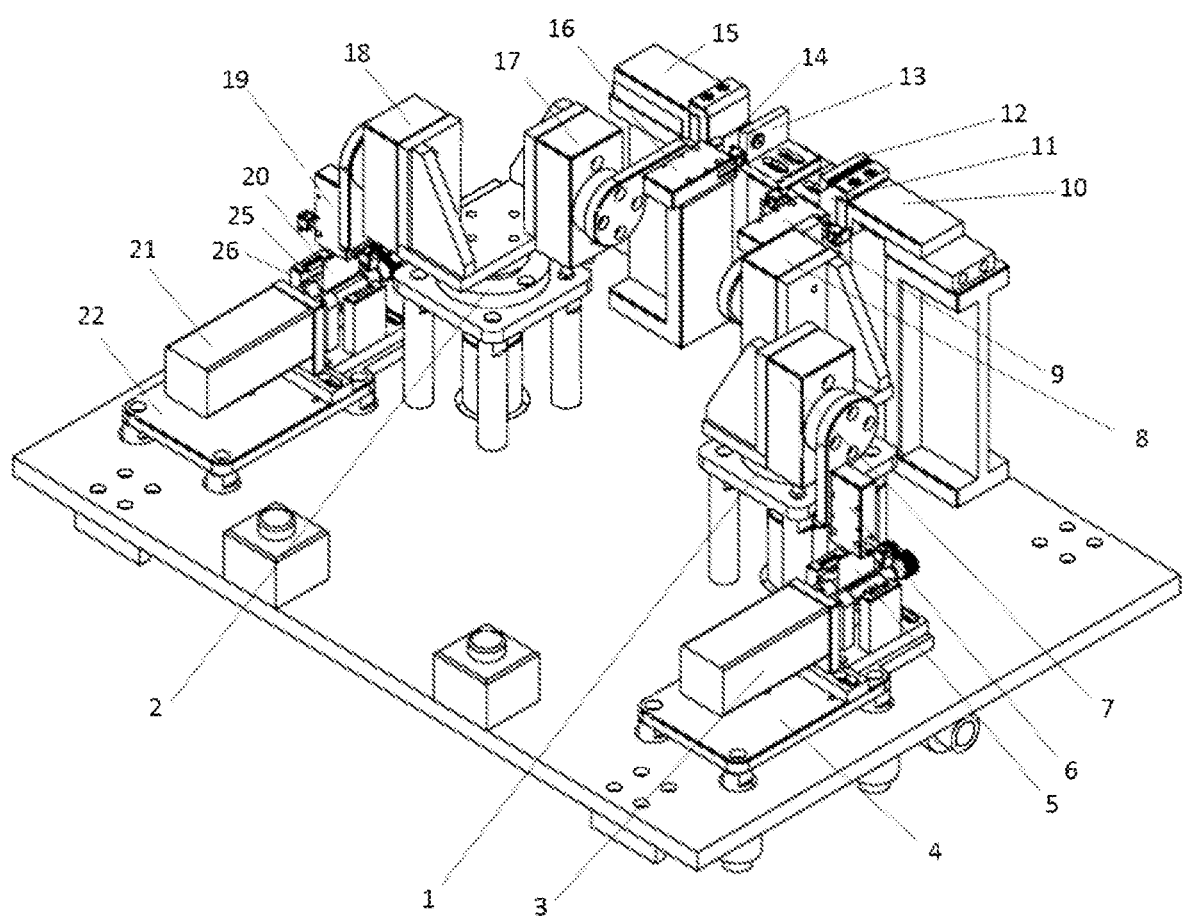
FIG. 1 is a schematic diagram of the present invention.
Figure 2:
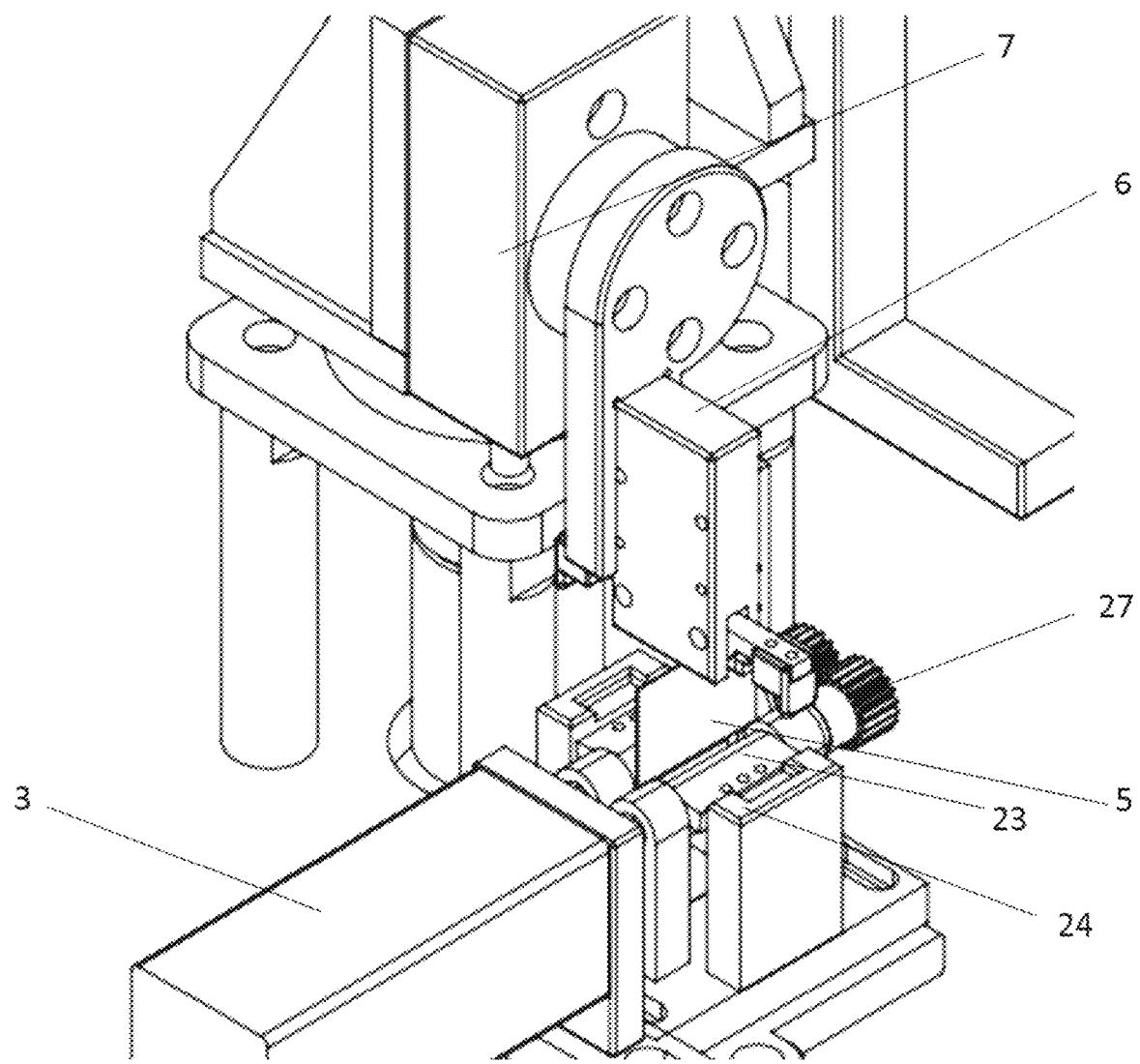
FIG. 2 is a partial enlargement of the automatic folding mechanism.
Figure 3:
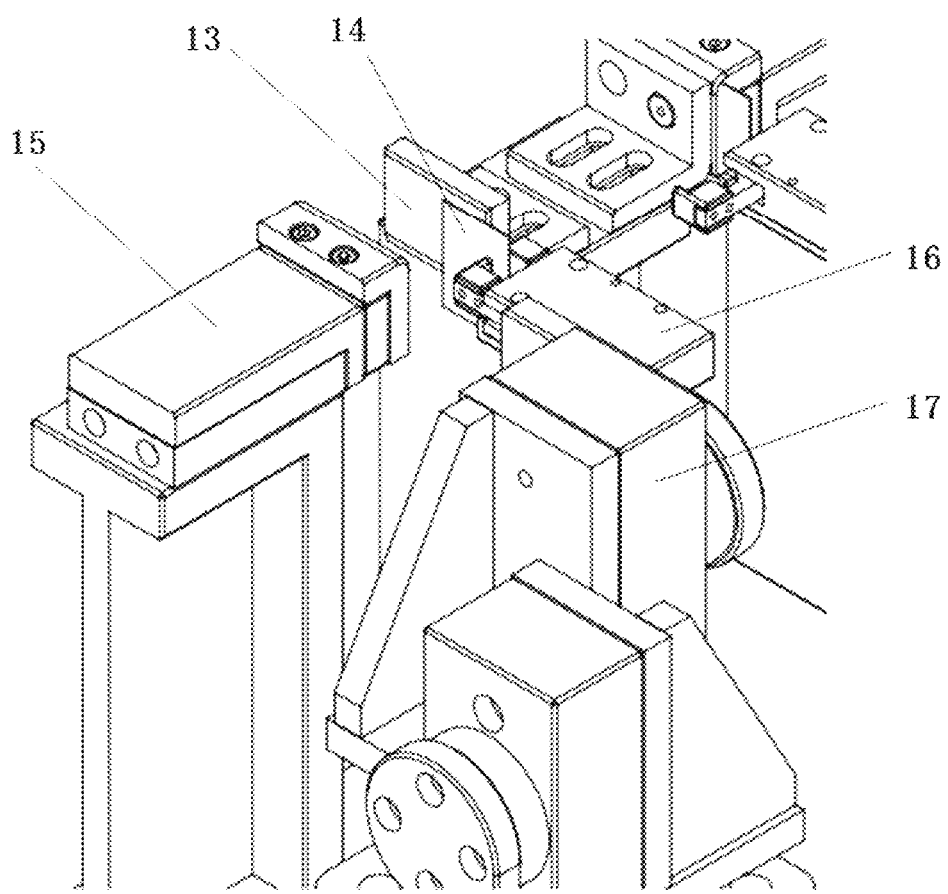
FIG. 3 is a partial enlargement diagram of the rotating mechanism and crease generating mechanism of the present invention.

In the figures, 1 first turntable; 2 second turntable; 3 first servo motor; 4 first lifting platform; 5 first metal sheets; 6 first finger cylinders; 7 first rotating cylinders; 8 second rotating cylinders; 9 second finger cylinders; 10 first pressing cylinders; 11 second metal sheets; 12 first electromagnetic support blocks; 13 second electromagnetic support blocks; 14 fourth metal sheets; 15 second pressing cylinders; 16 fourth finger cylinder; 17 fourth rotating cylinder; 18 third rotating cylinder; 19 third finger cylinder; 20 third metal sheet; 21 second servo motor; 22 second lifting platform; 23 first vacuum turning platform; 24 first sample positioning block; 25 second vacuum turning platform; 26 second sample positioning block.

DETAILED DESCRIPTION

The present invention is further described in detail below in connection with specific embodiments and with reference to the accompanying drawings.

As shown in the figures, the first set of rotating mechanism comprises the first turntable 1, the first metal sheet 5, the first finger cylinder 6, the first rotating cylinder 7, the second rotating cylinder 8, the second finger cylinder 9 and the second metal sheet 11.

The rotating arm is fixed above the first turntable 1. The two ends of the rotating arm are respectively fixed with the first rotating cylinder 7 and the second rotating cylinder 8. The two rotating cylinders are centrally symmetrical with the rotating arm. The first turntable 1 rotates to drive the two rotating cylinders to rotate. an output end of the first rotating cylinder 7 is fixed with the first finger cylinder 6, and an output end of the second rotating cylinder 8 is fixed with the second finger cylinder 9. The direction of the two finger cylinders is perpendicular to the horizontal plane. The rotating cylinder drives the finger cylinder to rotate 90° vertically, so that the finger cylinder is parallel to the horizontal plane.

The finger cylinder can clamp the sample on both sides of the metal sheet, and the metal sheet is in the middle of the folding sample to prevent the sample from bonding. The rotating cylinder makes the sample clamped by the finger cylinder rotate 90°, forming a state that the crease is perpendicular to the horizontal plane, so that the test results of the recovery angle test to be independent of the weight of the sample. The turntable transfers the sample from the automatic folding mechanism to the crease generating mechanism.

The second set of rotating mechanism comprises the second turntable 2, the fourth metal sheet 14, the fourth finger cylinder 16, the fourth rotating cylinder 17, the third rotating cylinder 18, the third finger cylinder 19 and the third metal sheet 20.

The first set of automatic folding mechanism comprises the first servo motor 3, the first lifting platform 4, the first vacuum turning platform 23 and the first sample positioning block 24.

The first servo motor 3 and the first sample positioning block 24 are fixed on the upper surface of the first lifting platform 4. The first sample positioning block 24 is located at the output end of the first servo motor 3 and below the first finger cylinder 6. The output end of the first servo motor 3 is fixed with a first vacuum turning platform 23, and the other ends of the first vacuum turning platform 23 are fixed with synchronous gears 27 separately. The first vacuum turning platform 23 are driven by the first servo motor 3 through the tooth engagement of synchronous gear 27; the second vacuum turning platform 23 are horizontally fixed above the first sample positioning block 24, and the metal sheet 5 is vertically fixed between them; the first vacuum turning platform 23 is square block, with air suction holes on one side of the square block, and the air suction holes are connected with the air suction fan. The sample is placed on the first vacuum turning platform 23, the suction holes absorb both sides of the sample to make the two sides of the sample aligned during the turning process of the first vacuum turning platform 23 to prepare for the accurate folding of the sample.

The first lifting platform 4 makes the sample placed on the surface of the first vacuum turning platform 23 rise to the position where the first finger cylinder 6 can clamp the sample. The vacuum turning platform achieves effective adsorption on both ends of the sample folding, thus forming the bending shape of the sample, and the sample positioning block plays the role of fixing the sample position.

The second set of automatic folding mechanism comprises the second servo motor 21, the second lifting platform 22, the second vacuum turning platform 25 and the second sample positioning block 26.

The first set of crease generating mechanism comprises the first pressing cylinder 10 and the first electromagnetic support block 12. The second pressing cylinder 15 and the second electromagnetic support block 13 are fixed above the crease bracket. The second pressing cylinder 15 and the second electromagnetic support block 13 are set correspondingly and at the level of the fourth finger cylinder 16 of the rotating mechanism. When the finger cylinder clamps the metal sheet and rotates 90° vertically, the metal sheet is located in the gap between the second pressing cylinder 15 and the second electromagnetic support block 13. Pressing cylinder is used to exert constant pressure on the sample. Electromagnetic support block is used to absorb the metal sheet, so that one side of the sample is clamped between the metal sheet and the electromagnetic support block, which plays the role of fixing the sample during the recovery test. The second set of crease generating mechanism comprises the second pressing cylinder 15 and the second electromagnetic support block 13.

A fabric automatic accurate folding method is described in the following steps:

Step 1: Place the first fabric sample of specified size in the first vacuum turning platform 23, and the second sample in the second vacuum turning platform 25. Open the measuring machine.

Step 2: The suction holes of the first vacuum turning platform 23 absorb both ends of the first sample.

Step 3: The first lifting platform 4 rises, and the first servo motor 3 drives the synchronous gear, which makes the first vacuum turning platform 23 turn over and drives the first sample to form a folding state.

Step 4: The first finger cylinder 6 holds both sides of the first sample folded together.

Step 5: The first vacuum turning platform 23 closes the vacuum, the first servo motor 3 drives the first vacuum turning platform 23 to turn in reverse to restore the open state, and the first lifting platform 4 descends.

Step 6: The first turntable 1 rotates 180°, and the first sample is held by the first finger cylinder 6 and transported to the position of the crease generating mechanism.

Step 7: The first rotating cylinder 7 rotates 90°, transfers the first sample into the pressure waiting area, and opens the electromagnet of the first electromagnetic support block 12. Thus, the first electromagnetic support block 12 absorbs the first metal sheet 5, then part of the first sample is stably clamped on the crease generating mechanism.

Step 8: The first pressure cylinder 10 is started to pressurize the first sample. At the same time, the first finger cylinder 6 is released, stopping holding the first sample.

Step 9: When the pressure time is reached, the first pressing cylinder 10 is released, the first electromagnetic support block 12 still absorbs the first metal sheet 5, the first sample is in the state of free recovery of creases, and the camera records the state of the recovery process of the first sample.

Step 10: When the first sample is free to recover for a period of time, the first electromagnet is released by the electromagnet of block 12, and the first rotating cylinder 7 rotates 90° to return to its initial state.

Step 11: When the first sample is pressurized, the second sample is in the second vacuum turning platform 25, and the suction holes of the second vacuum turning platform 25 absorb both ends of the second sample.

Step 12: The second lifting platform 22 rises, and the second servo motor 21 drives the synchronous gear, which makes the second vacuum turning platform 25 turn over and drives the second sample to form a folding state.

Step 13: The third finger cylinder 19 holds both sides of the second sample folded together.

Step 14: The second vacuum turning platform 25 closes the vacuum, the second servo motor 21 drives the second vacuum turning platform 25 to turn in reverse to restore the open state, and the second lifting platform 22 descends.

Step 15: The second turntable 2 rotates 180°. The second sample is held by the third finger cylinder 19 and transported to the position of crease generating mechanism.

Step 16: The third rotating cylinder 18 rotates 90°, transfers the second sample into the pressure waiting area, opens the electromagnet of the second electromagnetic support block 13 at the same time, makes the second electromagnetic support block 13 absorb the third metal sheet 20, then part of the second sample is stably clamped on the crease generating mechanism.

Step 17: The second pressing cylinder 15 is started to pressurized the second sample. Meanwhile, the third finger cylinder 19 is released, stopping holding the second sample.

Step 18: In the process of pressing the second sample, the first sample is tested and the whole test platform is shifted so that the second sample can enter the camera field of vision.

Step 19: When the second sample reaches the pressure time, the second pressing cylinder 15 is released, the second electromagnetic support block 13 still absorbs the third metal sheet 20, and the second sample is in the state of free recovery of creases. The camera records the recovery process of the second sample.

Step 20: After the free recovery of the second sample for a period of time, the electromagnet of the second electromagnetic support block 13 is released, and the third rotating cylinder 18 rotates 90° to return to its initial state.

Step 21: When the first lifting platform 4 descends, the third sample can be placed in the first vacuum turning platform 23.

Step 22: The suction holes of the first vacuum turning platform 23 absorb both ends of the third sample.

Step 23: The first lifting platform 4 rises, and the first servo motor 3 drives the synchronous gear, which makes the first vacuum turning platform 23 turn over and drives the third sample to form a folding state.

Step 24: The second finger cylinder 9 holds both sides of the third sample folded together.

Step 25: The first vacuum turning platform 23 closes the vacuum, the first servo motor 3 drives the first vacuum turning platform 23 to turn in reverse, to restore the open state, and the first lifting platform 4 descends.

Step 26: The first turntable 1 rotates 180°, and the third sample is held by the second finger cylinder 9 and transported to the position of the crease generating mechanism.

Step 27: The second rotating cylinder 8 rotates 90°, transfers the third sample into the pressure waiting area, and opens the electromagnet of the first electromagnetic support block 12, so that the first electromagnetic support block 12 absorbs the second metal sheet 11, then part of the third sample is stably clamped on the crease generating mechanism.

Step 28: The first pressure cylinder 10 is started to pressurize the third sample. Meanwhile, the second finger cylinder 9 is released, stopping holding the third sample.

Step 29: During the third sample pressurization process, the second sample is tested, and the whole test platform is shifted back to its original position, so that the third sample can enter the camera field of vision.

Step 30: After the third sample reaches the pressure time, the first pressing cylinder 10 is released, the first electromagnetic support block 12 still absorbs the second metal sheet 11, and the third sample is in the state of free recovery of creases. The camera records the recovery process of the third sample.

Step 31: When the third sample is restored freely for a period of time, the electromagnet of the first electromagnetic support block 12 is released, and the second rotating cylinder 8 rotates 90° to return to its initial state.

Step 32: When the second lifting platform 22 descends, the fourth sample can be placed in the second vacuum turning platform 25 and tested according to this method.

The invention claimed is:

1. An automatic fabric folding device comprising a rotating mechanism, an automatic folding mechanism and a crease generating mechanism; the automatic folding mechanism is located below a first finger cylinder on one side of the rotating mechanism, and a second finger cylinder on the other side of the automatic folding mechanism is adjacent to a crease generating mechanism;

the rotating mechanism comprises a first turntable, a first metal sheet, the first finger cylinder, a first rotating cylinder, a second rotating cylinder, the second finger cylinder and a second metal sheet;

a rotating arm is fixed above the first turntable; the first rotating cylinder and the second rotating cylinder are fixed at both ends of the rotating arm respectively; the two rotating cylinders are centrally symmetrical with the rotating arm; the first turntable rotates to drive the two rotating cylinders to rotate; an output end of the first rotating cylinder is fixed with the first finger cylinder, and an output end of the second rotating cylinder is fixed with the second finger cylinder, the first rotating cylinder is adapted to rotate the first finger cylinder between a vertical and a horizontal orientation, and the second rotating cylinder is adapted to rotate the second finger cylinder between a vertical and a horizontal orientation;

the finger cylinders, including the first and second finger cylinders, can clamp a sample comprising fabric on both sides of the corresponding metal sheet; the metal sheets, such as the first and second metal sheets, are in the middle of the sample as it is folded to prevent the sample from bonding; the rotating cylinders, such as the first and second rotating cylinders, make the sample clamped by the corresponding finger cylinder rotate 90°, forming a state that the sample is perpendicular to the horizontal plane, so that a test result of recovery angle, i.e. an angle between two folded fabric wings, is not affected by the weight of the sample when the recovery angle is tested; the first turntable transports the sample from its adjacent automatic folding mechanism to the corresponding crease generating mechanism; the second turntable transports the sample from its adjacent automatic folding mechanism to the corresponding crease generating mechanism;

the automatic folding mechanism comprises a servo motor, a lifting platform, a first vacuum turning platform and a first positioning block;

the servo motor and the sample positioning block are fixed on the upper surface of the first lifting platform, and the sample positioning block is located at an output end of the servo motor and below the first finger cylinder; the output end of the servo motor is fixed with the first vacuum turning platform, and the other ends of the first and second vacuum turning platforms are fixed with a synchronous gear; and the first vacuum turning platform is driven by the servo motor through the synchronous gear; the first vacuum turning platform is adjacent to the sample positioning block and the first metal sheet is vertically fixed between them; the first vacuum turning platform is a square block, with an air suction hole on one side of the square block, and the air suction hole is connected with an air suction fan; there are three holes on the other side of the first vacuum turning platform; the sample is placed on the three holes side of the first vacuum turning platform; there are three holes on the second vacuum turning platform the suction holes on the first vacuum turning platform hold a first side of the sample and the suction holes on the second vacuum turning platform hold the second side of the sample fabric to make the two sides of the sample aligned during a turning process of the first vacuum turning platform;

the crease generating mechanism includes a pressing cylinder and an electromagnetic support block; the pressing cylinder and the electromagnetic support block are fixed above a crease bracket, and the pressing cylinder and the electromagnetic support block are correspondingly arranged and parallel to the top of the first finger cylinder of the rotating mechanism; when the first finger cylinder holds the first metal sheet and rotates up 90°, the first metal sheet is located in a gap between the pressing cylinder and the electromagnetic support block.

2. A method of using the automatic fabric folding device of claim 1 comprising the following steps:

step 1: place the sample on an upper surface of the first vacuum turning platform, wherein the three holes on the first vacuum turning platform hold the first side of the sample and the three holes on the second vacuum turning platform hold the second side of the sample;

step 2: the lifting platform rises, and the servo motor drives the synchronous gear to turn the first vacuum turning platform, which drives the sample to form a folded state; the first metal sheet is located between the folded sides of the sample;

step 3: the first finger cylinder holds two different ends of the same sample;

step 4: the vacuum to the air suction holes is turned off, the servo motor drives the first vacuum turning platform to turn in reverse to restore an open state, and the lifting platform descends;

step 5: the first turntable rotates 180°, and the sample is held by the first finger cylinder and transported to the crease generating mechanism;

step 6: the first rotating cylinder rotates 90°; the sample is placed between pressing cylinder and the electromagnetic support block; the electromagnetic support block is opened so that the electromagnetic support block can receive the first metal sheet; then part of the sample is stably clamped on the crease generating mechanism;

step 7: the pressing cylinder presses the sample, and the first finger cylinder releases its hold on the sample;

step 8: after a predetermined period of time, the electromagnetic support block is turned off, the electromagnetic support block still holds the first metal sheet, the sample is in a state of free recovery of creases, step 9: when the sample is recovered freely for a period of time, an electromagnet of the electromagnetic support block is released, and the first rotating cylinder rotates 90° to return to its initial state;

step 10: the lifting platform descends, a next sample can be placed on the upper surface of the first vacuum turning platform.

\* \* \* \* \*